(12) United States Patent
Masculo et al.

(10) Patent No.: US 11,341,834 B2
(45) Date of Patent: May 24, 2022

(54) FALL DETECTION

(71) Applicant: Lifeline Systems Company, Framingham, MA (US)

(72) Inventors: Felipe Maia Masculo, Eindhoven (NL); Warner Rudolph Theophile Ten Kate, Waalre (NL)

(73) Assignee: Lifeline Systems Company, Framingham, MA (US)

( * ) Notice: Subject to any disclaimer, the term of this patent is extended or adjusted under 35 U.S.C. 154(b) by 0 days.

(21) Appl. No.: 17/111,563

(22) Filed: Dec. 4, 2020

(65) Prior Publication Data

US 2021/0183225 A1 Jun. 17, 2021

(30) Foreign Application Priority Data

Dec. 11, 2019 (EP) .................................. 19215279

(51) Int. Cl.
G08B 23/00 (2006.01)
G08B 21/04 (2006.01)
A61B 5/11 (2006.01)

(52) U.S. Cl.
CPC ........ *G08B 21/0446* (2013.01); *A61B 5/1117* (2013.01); *A61B 2562/0219* (2013.01)

(58) Field of Classification Search
CPC ... A61B 5/0022; A61B 5/7275; A61B 5/1112; A61B 2562/0219; G08B 21/0446
See application file for complete search history.

(56) References Cited

U.S. PATENT DOCUMENTS

| 8,732,100 B2 | 5/2014 | Blowers et al. |
| 10,335,059 B2* | 7/2019 | Annegarn .......... G08B 21/0446 |
| 2008/0129518 A1* | 6/2008 | Carlton-Foss ......... G08B 25/10 340/573.1 |
| 2012/0050031 A1* | 3/2012 | Ten Kate ................ G08B 21/04 340/539.11 |
| 2012/0314901 A1* | 12/2012 | Hanson .................. G08B 21/02 382/103 |
| 2017/0109990 A1* | 4/2017 | Xu ........................ G08B 21/043 |
| 2017/0337339 A1* | 11/2017 | Cronin ................. A61B 5/7275 |
| 2019/0019581 A1* | 1/2019 | Vaughan ................ A61B 5/486 |
| 2020/0337570 A1* | 10/2020 | Valenti ................. A61B 5/7257 |

FOREIGN PATENT DOCUMENTS

| EP | 3346402 A1 | 11/2018 |
| WO | 2015036245 A1 | 3/2015 |

OTHER PUBLICATIONS

International Search Report and Written Opinion, International Application No. PCT/EP2020/085195, dated Feb. 12, 2021.

* cited by examiner

*Primary Examiner* — Julie B Lieu
(74) *Attorney, Agent, or Firm* — Honigman LLP

(57) ABSTRACT

Proposed are concepts for distinguishing between fall events and non-fall-events for different sub-groups of subjects within a monitored group (i.e. monitored population) of subjects. It is proposed that an entire group/population of monitored subjects may be partitioned into sub-groups, each sub-group consisting of a plurality of members (i.e. subjects) having a certain property value or characteristic unique to that group. A respective decision value may be determined for each sub-group, wherein the decision value for a sub-group takes account of a previously obtained false fall detection rate for that sub-group.

13 Claims, 3 Drawing Sheets

FALL DETECTION

CROSS-REFERENCE TO PRIOR APPLICATIONS

This application claims the benefit of European Patent Application No. 19215279.1, filed on 11 Dec. 2019. This application is hereby incorporated by reference herein.

FIELD OF THE INVENTION

The invention relates to the field of fall detection, such as fall detection employed in Personal Emergency Response Systems for example.

BACKGROUND OF THE INVENTION

Personal Emergency Response Systems (PERS) enable elderly and disabled people to live independently by summoning immediate help when an adverse event, such as a fall, occurs. The use of such systems allows people who would otherwise require round-the-clock care to live in their own homes, and reduces their care costs.

Some PERS systems rely on subject input, such as a button press, to raise an alarm when assistance is required, but this means that a subject is unable to access immediate medical help in the case of the subject becoming unconscious as a result of a fall, when such help is most critical. There is also a risk that the subject may fall in such a way that, while remaining conscious, he/she is unable to activate the alarm.

For these reasons, automatic fall detection systems have been developed that can summon help without needing subject input. These detection systems generally come in the form of wearable devices that contain sensors to monitor subjects' movements and processors that decide whether a detected movement is the result of a fall. However, current automatic fall detection systems are not able to distinguish with complete accuracy between falls and movements that occur during everyday activities. For example, fall detection accuracy is particularly low in wrist-worn devices.

In order to avoid failing to detect genuine falls, fall detection systems may be configured to have a high false detection rate (i.e. the rate of non-fall events classified as fall events) so as to minimize the number of falls that are not detected as such. A high false alarm rate necessitates the use of a cancel function to avoid summoning help needlessly; subjects can activate this function when the fall detector incorrectly detects a fall. However, some subjects may find the cancel function difficult to use, become panicked when a false alarm occurs and forget to activate the cancel function, or accidentally activate the cancel function when a genuine fall has occurred.

There is therefore a need for fall detection concepts that are able to detect most actual fall events while keeping the number of false alarms to a minimum. However, these two requirements are contradictory, because it is typically only possible to increase the detector's true positive rate (i.e. detection of actual falls) at the cost of having a higher rate of false alarms.

SUMMARY OF THE INVENTION

The invention is defined by the claims.

According to examples in accordance with an aspect of the invention, there is provided a computer-based method for distinguishing between a fall event and a non-fall-event for a plurality of subjects.

The method comprises: obtaining first and second false fall detection rates for first and second sub-groups of the plurality of subjects, respectively, and wherein the first and second sub-groups comprise subjects with first and second differing values of a property of the plurality of subjects, respectively; determining, based on the first false fall detection rate, a first decision value for distinguishing between a fall event and a non-fall-event of subjects of the first sub-group; and determining, based on the second false fall detection rate, a second decision value for distinguishing between a fall event and a non-fall-event of subjects of the second sub-group.

Proposed are concepts for determining different decision values (e.g. threshold values) for distinguishing between fall events and non-fall-events for different sub-groups of subjects within a monitored group (i.e. monitored population) of subjects. In this way, a property or characteristic specific to a group of monitored subjects (which may influence a false fall detection rate) may be accounted for, thereby providing for adjusted or tailored event classification that leads to improved fall detection accuracy. Embodiments may therefore dynamically determine and adapt decision values (used for fall event detection) to different sub-groups of a monitored subject population.

Embodiments may therefore achieve a larger true positive detection rate, on average, while keeping an overall false alarm rate below an acceptable maximum.

For instance, it may be proposed that an entire group/population of monitored subjects is partitioned into sub-groups, each sub-group consisting of a plurality of members (i.e. subjects) having a certain property value or characteristic unique to that group. A respective decision value may be determined for each sub-group, wherein the decision value for a sub-group takes account of a previously obtained false fall detection rate for that sub-group.

By way of example, location-specific factors may contribute to the number of false alarms (i.e. false fall detections). For instance, it has been observed that variations of atmospheric pressure, e.g. due to storms, may have a significant impact on the false alarm rate of an affected location. Such factors may therefore be taken account of by defining sub-groups according to subject location and then determining a decision value for each sub-group, the decision value for each sub-group being determined so that a false fall detection rate for subjects of that sub-group equal a predetermined acceptable rate for example.

By way of further example, subject activity, fall risk, age, weight or medical conditions may be used to define sub-groups of monitored subjects.

Proposed concepts may therefore an improved (higher) true positive detection rate across an entire monitored group/population of subjects, while maintaining an overall false alarm (i.e. false fall detection) rate below a predetermined acceptable maximum. Such concepts may, for example, dynamically adapt a classification decision value to different sub-groups of the monitored group/population of subjects. A wide-range of properties of the subjects may be used to define sub-groups of the monitored group/population of subjects. In this way, proposed embodiments may take account of a variety of different properties/characteristics of subjects that may impact false alarm rates.

Unlike conventional fall detection concepts, which may employ a fixed fall detection decision value for all monitored subjects, proposed concepts can determine different fall detection decision values for different sub-groups of the monitored subjects. Such sub-groups may be defined based on properties or characteristics of the monitored subjects, e.g. by splitting the monitored subjects into sub-groups based on their location or age. For instance, each subject of a first sub-group may have the same first value of a property, and each subject of a second sub-group may the same second value of the property, the first value being different from the second value.

Embodiments may ensure that the fall detection decision values are within certain limits so to ensure a minimum detection probability. However, the variation of decision values across different sub-groups of a monitored population may be such that the average over the sub-groups results in an improved fall detection accuracy (i.e. a reduced likelihood of false alarms being generated when a subject has not actually fallen).

In some embodiments, determining the first decision value may comprise determining a value at which a false fall detection rate for subjects of the first sub-group is equal to a predetermined rate, a false detection rate being a rate at which non-fall events are determined to be fall events. For instance, the predetermined rate may be defined so as to maintain a predetermined minimum detection probability value. In this way, the value of a decision for a sub-group may be optimized so as to ensure a minimum detection sensitivity is achieved whilst ensuring that false detections are reduced or minimized.

Further, the first and second decision values may be determined so as to maintain an overall false fall detection rate across the first and second groups remains constant whilst the an average true positive detection rate is increased.

The first decision value may be associated with each subject of the first sub-group. Similarly, the second decision value may be associated with each subject of the second sub-group. Put another way, the first sub-group may be assigned the first decision value, and the second sub-group may be assigned the second decision value. This may enable the decision value for each monitored subject of the entire monitored population to be individually assigned/allocated based on the sub-group it belongs to.

In some embodiments, the first and second false fall detection rates for first and second sub-groups may be obtained from a separate and/or remotely-located information source (e.g. a fall detection system, database of fall cases, subject monitoring system, etc.). In this way, embodiments may be configured to simply receive information about fall detection rates for a monitored population of subjects, and then employ the received information to determine decision values for different sub-groups of the monitored population. Proposed embodiments may therefore information from existing fall monitoring or detection systems in order to dynamically and flexibly determine different decision values for distinguishing between fall events and non-fall-events of different sub-groups of monitored population of subjects. Embodiments may increase a value of existing/conventional fall detection systems by providing modified and/or extended functionality.

Conversely, other embodiments may be configured to determine the first and second false fall detection rates for first and second sub-groups. For example, an embodiment may comprise: identifying the first and second sub-groups of the plurality of subjects; monitoring the plurality of subjects to detect potential fall events; for each detected potential fall event, distinguishing between the detected potential fall event being a fall event and a non-fall-event based on a fall detection algorithm employing a decision value; and determining first and second false fall detection rates based on the identified first and second sub-groups and the results of distinguishing the potential fall events between being fall events and non-fall-events. Thus, rather than relying on information about monitored subjects from a separate monitoring system, embodiments may be configured to monitoring subjects in order to detect potential fall event and determine false fall detection rates. For instance, an embodiment may comprise a subject monitoring system or a PERS system with improved or extended functionality provided as a result of the proposed concept(s). Purely by way of further example, an embodiment may comprises a PER system that is adapted to define sub-groups of a monitored population of subjects and to implement different fall detection decision values for the different sub-groups.

According to some embodiments, the fall detection rate for a sub-group of the plurality of subjects may be based on a ratio between a number of false fall detections for the sub-group and the number of subjects in the sub-group. In this way, embodiments may take account of sub-group size (i.e. the number of members of a sub-groups), so as to provide a relatively consistent and comparable measure across sub-groups of differing sizes.

By way of example, wherein the property of the plurality of subjects may comprises: location; activity; fall risk; age; medical condition; weight; gender, diagnosis; disease; prescription; equipment/aids used, etc. Various properties or characteristics of the monitored subjects may therefore be used to group the subjects into sub-groups, and the properties/characteristics may be physiological (and fixed or slow changing) and/or situational (and thus variable with respect to time). Such properties/characteristics may directly (or indirectly) influence a false fall detection rate, and so proposed embodiments may account for this by defining groups based on these properties/characteristics and then determining different decision values for the different groups. Proposed embodiments may therefore leverage a realisation that a property of a monitored subject may influence or affect a false fall detection rate. By modifying a decision value to account for such a dependency on the property, embodiments may adapt the decision value to provide more accurate fall detection (e.g. enable the distinguishing between a fall event and a non-fall-event such that false fall detection rate is reduced whist ensuring that true positives are detected). In this way, the decision value may be customized to a group of subjects to ensure that the false alarm rate for that group of subjects is at an acceptable level.

According to examples in accordance with an aspect of the invention, there is provided a computer program comprising code means for implementing the method of any previously described method when said program is run on a processing system.

According to a concept of the invention, there is provided a system for distinguishing between a fall event and a non-fall-event for a plurality of subjects. The system comprises: an interface component adapted to obtain first and second false fall detection rates for first and second sub-groups of a plurality of subjects, respectively, and wherein the first and second sub-groups comprise subjects with first and second differing values of a property of the plurality of subjects, respectively; and a decision value calculation unit adapted to determine, based on the first false fall detection rate, a first decision value for distinguishing between a fall event and a non-fall-event of subjects of the first sub-group, and to determine, based on the second false fall detection rate, a second decision value for distinguishing between a fall event and a non-fall-event of subjects of the second sub-group.

It may be preferable, to define the (at least) two decision values such that the total false fall detection rate, of all the combined groups, is below a certain predetermined acceptable value. Such optimization of the decision value may be undertaken so as to maximize the lowest fall detection probability (i.e. sensitivity) over the groups, or to maximize their average, etc.

There is also proposed a system for detecting a fall of a subject, comprising: one or more sensors for obtaining movement data responsive to a subject's movement; and the system for distinguishing between a fall event and a non-fall-event for a plurality of subjects according to a proposed embodiment, further configured to: receive the movement data from the one or more sensors; detect a potential fall event based on the movement data; determine which sub-group the subject is a member of; and classify the detected potential fall event as a fall event or a non-fall event by comparing information associated with the fall event with the decision value for the sub-group the subject is determined to be a member of.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
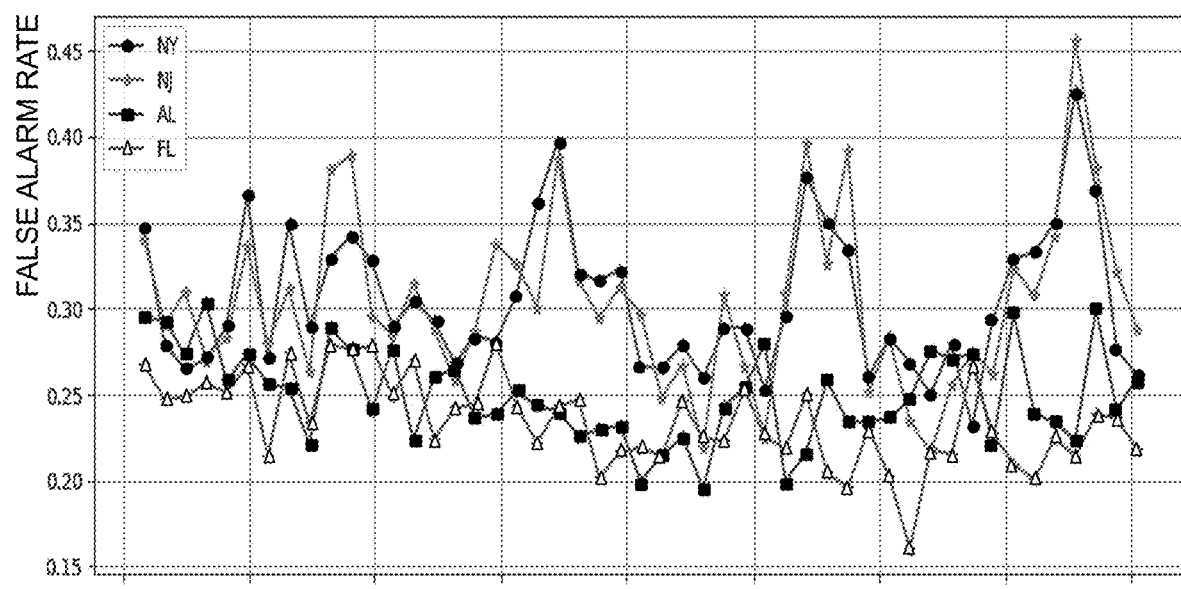
FIG. 1 depicts a variation in false fall detection rate over time for four different states in America.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

It should be understood that the Figures are merely schematic and are not drawn to scale. It should also be understood that the same reference numerals are used throughout the Figures to indicate the same or similar parts.

Existing fall detection systems typically consist of two phases. In a first phase, values for parameters that may indicate the likelihood of a fall are obtained for an event from data from sensors such as accelerometers and barometric sensors. Other sensors may include gyroscopes, magnetometers, ultrasound sensors, radar sensors, skin conductivity sensors and pulse (photoplethysmography, PPG) sensors, for example. The parameters may include any of height, height change, orientation, orientation change, velocity, duration and impact. Other example values include distance to ground (or ceiling) and physiological quantities such as heart rate, respiration rate, voice quality (anxiety, specific utterances) and other sounds. Events are typically defined using a trigger, which monitors at least one trigger parameter: an event is considered to have occurred at the point at which the value of a trigger parameter exceeds or falls below a corresponding predetermined trigger decision value (or when a change of a value is greater than a predetermined change). For example, an event may be detected when the barometer indicates a height drop of more than 50 cm, or the accelerometer indicates an acceleration of more than $2*g$. Such designs typically make use of advanced machine learning techniques, e.g. deep learning. In those approaches, a (deep) neural network directly takes the sensor signals (samples) as an input. The window of samples might be centred around a trigger, but the window may also move over the input nodes of the neural net (i.e. all samples shift one or more nodes further; the latest samples dropping off and new samples entering).

In a second phase, a classifier (e.g. a processing device) takes one or more of the obtained parameter values from the event and outputs a value indicating or predicting whether or not the event is a fall. In some cases, the obtained parameter value(s) are used to calculate a probability that a fall has occurred, e.g. using a fall event probability distribution, and the classifier applies a decision to the calculated probability to decide whether that probability is predict, with a certain degree of accuracy, whether or not a fall has occurred. For example, the output of a neural net can be treated as a probability value, and by comparison with a decision value, the event (sample set at the input window) is determined to be a fall or non-fall event. An alternative approach may be determine a likelihood ratio between likelihood an event is a fall and likelihood the event is a non-fall. In this case, classification of an event also employs a decision to decide whether a given event is a fall or a non-fall.

According to a concept of the invention, there is proposed a method and system for distinguishing between a fall event and a non-fall-event for a plurality of subjects. The concept includes obtaining first and second false fall detection rates for first and second sub-groups of the plurality of subjects, respectively. Based on the first and second false fall detection rates, first and second decision values for the first and second sub-groups, respectively, are then determined. In this way, the decision values may be adapted per sub-group.

Embodiments are at least partly based on the realization that a property or characteristic of a subject may affect the false detection rate. By separating the monitored population of subjects into a plurality sub-groups (e.g. two or more sub-groups) based on such a property/characteristic, a decision value used to distinguish between a fall event and a non-fall-event may be adapted to each of a plurality of sub-groups. In this way, a property/characteristic specific to a group of monitored subjects (which may influence a false fall detection rate) may be accounted for, thereby providing for adjusted or tailored fall event classification that leads to improved fall detection accuracy.

Illustrative embodiments may, for example, be employed in (or in conjunction with) fall detectors and/or fall detection systems. Such detectors and/or systems may be used in PERS systems at a subject's home or in specialized accommodation such as Senior Living Facilities, in hospital products, and/or using apps designed for smartwatches.

Proposed is an approach for enabling the dynamic modification of a decision value to a group of subjects having the same property or characteristic. Such proposals may thus facilitate simple adaptation of a decision value to cater for a specific property or characteristic of a sub-group of subjects that can influence a false fall detection rate for that sub-group, and this may for example be done in consideration of a target false detection rate and/or minimum detection probability.

Embodiments of the present invention may therefore be directed toward improving the accuracy and/or functionality of a fall detection systems.

By way of example only, illustrative embodiments may be utilized in many different types of clinical, medical or subject-related environments, such as a hospital, doctor's office, ward, care home, person's home, etc.

As mentioned above, proposed concepts are at least partly based on the realization that a property or characteristic of a subject may affect the false fall detection rate. Purely by way of example, one such property of a subject may be location of the subject. To demonstrate this, FIGS. 1 and 2 illustrate exemplary data demonstrating how location-specific factors may contribute to false fall detection rate.

FIG. 1 depicts a variation in false fall detection rate over time for four different states in America (namely: NY, NJ, AL and FL). Time, in months, is represented on the horizontal (X-) axis, and the number of false fall detections per month (i.e. false fall detection rate) is represented on the vertical (Y-) axis.

From FIG. 1, it can be observed that the false fall detection rate can change significantly over time. Moreover, the false fall detection rate patterns are similar between neighbouring states, but differ between states that are distant.

Figure 2:
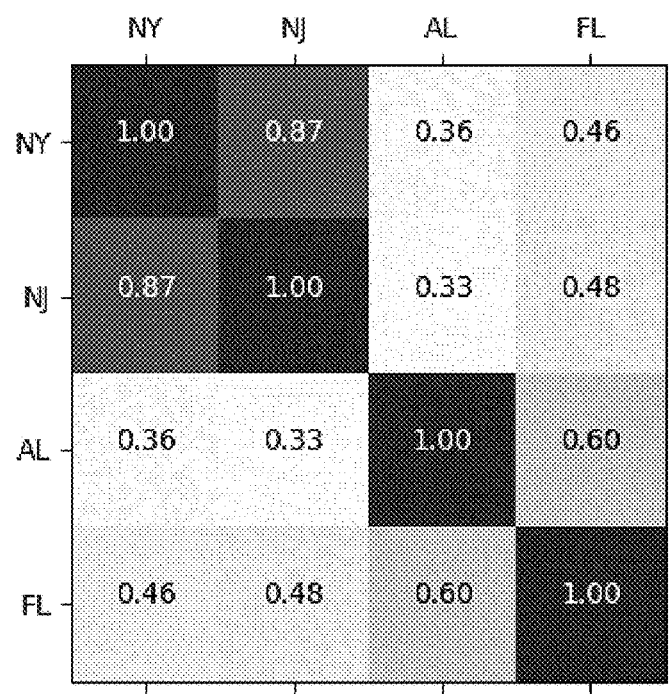
FIG. 2 shows a correlation matrix between the false alarm rates of the four different states in America.

This is also confirmed by FIG. 2 which shows a correlation matrix between the false alarm rates of the four different states in America (NY, NJ, AL and FL). From FIG. 2 is can be seen that the correlation between false alarm rates of neighbouring states is higher. In other words, neighbouring states show higher correlation than distant states.

Based on such a realisation that the false fall detection rate can be dependent upon the location of a subject, it is proposed to implement location-based monitoring of the false fall detection and modify a decision value for distinguishing between a fall event and a non-fall-event according to subject location. In particular, the decision value may be defined for a particular location such that the overall false fall detection remains constant whilst the (average) true positive rate is improved (compared to when setting one (worst-case) decision value for the whole population). By way of example, this may be achieved by increasing the fall detection decision value in the locations experiencing a high false fall detection rate, which may then also enable the decrease of the decision value for other locations where the false fall detection rate is lower for example.

By way of example, an embodiment employing the concept of using location to groups subject may comprise the following main stages:

(i) Group monitored subjects into sub-groups based on location information;

(ii) Monitor the false fall detection rate of the fall detection algorithm for each sub-groups;

(iii) For each sub-group, calculate a fall detection decision value based on the false fall detection rate and number of subjects of the sub-group;

(iv) Update the fall detection decision value for all subject according to their assigned sub-group.

Although the above-detailed examples employ location information to define sub-groups, other properties or characteristics of subjects may influence false fall detection rates and thus be used to define sub-groups. For example, in alternative embodiments, a plurality of sub-groups may be defined based on other subject properties such as subject activity, subject behaviour, subject age, subject gender, subject medical diagnosis, etc.

Figure 3:
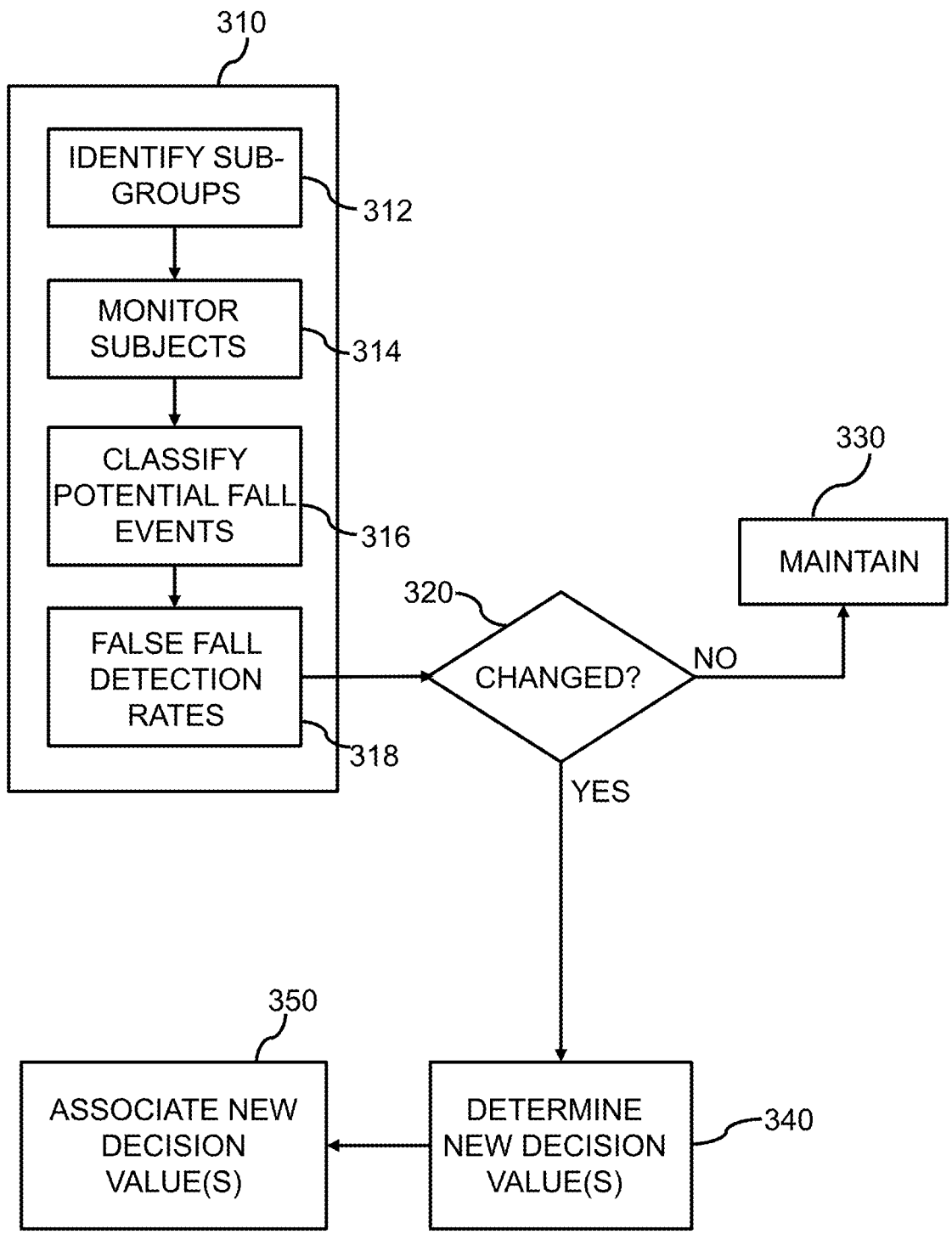
FIG. 3 is a flow diagram of a method for distinguishing between a fall event and a non-fall-event for a plurality of subjects according to a proposed embodiment.

FIG. 3 illustrates a method for distinguishing between a fall event and a non-fall-event for a plurality of subjects according to a proposed embodiment. Such a method may be used to determine fall detection decision values that may be used by a fall detection algorithm in order to distinguish between a fall event and a non-fall-event for a plurality of subjects (i.e. to classify a potential fall event as either a fall event or a non-fall-event).

The method begin with step 310 of obtaining at least first and second false fall detection rates for at least first and second sub-groups of the plurality of subjects, respectively.

Here, by way of explanation, a false fall detection rate is a rate at which non-fall events are determined by the system to be fall events. A false fall detection rate may therefore be thought of as a false alarm rate and may, for example, be measured as the number of false fall detections per unit time (e.g. per hour, per day, per month, etc.) or number of false fall detections per subject.

Also, in this example, the first and second sub-groups comprise subjects with first and second differing values of a property of the plurality of subjects, respectively. Put another way, the first sub-group comprises a plurality of subjects each having a first value for a property of a subject (e.g. first geographic location, age between 20-30 years, male gender, etc.) and the second sub-group comprises a plurality of subjects each having a second, different value for the property (e.g. second geographic location, age between 40-50 years, female gender, etc.).

Simply by way of example, the property of the subjects may comprise: subject location; activity; fall risk; age; medical condition; weight; gender, etc. Thus, it will be appreciated that any one of a range of physiological, physical, fixed or variable properties may be used to define sub-groups in the total population of the plurality of subjects. Thus, although the example is described as having two sub-groups, it will be appreciated that the number of sub-groups may be greater than two in other embodiments.

In the embodiment of FIG. 3, the step 310 of obtaining first and second false fall detection rates comprises a set of sub-steps 312 to 318 which are executed to obtain the first and second false fall detection rates.

Specifically, step 312 comprises identifying the first and second sub-groups of the plurality of subjects (e.g. by grouping the subjects into two sub-groups based on their value of the property). A sub-group identifier is then assigned to every subject according to their value of the property. In this example embodiment, the subjects are based on their geographical location (e.g. obtained from their address information). The resolution of the location information may be, for example, a zip code, city, state, etc. Of course, it will be appreciated that, in other embodiments, the sub-groups may be defined based on other parameters, such as activity, fall risk, age, gender, medical conditions or other relevant criteria.

Step 314 then comprises monitoring the plurality of subjects to detect potential fall events. For each detected potential fall event, the detected potential fall event is distinguished between being a fall event and a non-fall-event based on a fall detection algorithm in step 316. In other words, step 316 comprises classifying each potential fall events as either a fall event or a non-fall-event. Using the results from step 316, first and second false fall detection rates for the first and second sub-groups, respectively, are determined in step 318.

By way of example, one approach to determining a false fall detection rate is to use the overall fall detection rate of the algorithm as an approximation of the false fall detection rate. This may be acceptable because, typically, the false fall detection rate is much higher than the true fall detection rate.

Another approach to determine a false fall detection rate is to use another source of information to either confirm or correct the output of the fall detection algorithm. This other source of information could, for example, be the data logged by a call centre agent who contacts the subject whenever a fall is detected and determines, based on a response from the subject, whether or not a fall did happen. Alternatively, or additionally, detected falls which are cancelled (e.g. marked/indicated to not be falls) by the subject may be tracked.

Purely by way of example, each false fall event occurrence is paired with the sub-group assigned to the subject that generated the false fall event. The false fall detection rate per group can then be computed by taking the ratio between the number of false fall event for a given sub-group and the number of active subjects in that sub-group.

In some other embodiments, a confidence interval may be computed for the false alarm rate per group. This can be done, for example, using a Poisson distribution to model the number of false alarms per group and applying a confidence interval formula for the rate parameter.

After determining the first and second false fall detection rates in step 310, the method proceeds to step 320, wherein it is determined if the fall detection rates have changed compared to previous or estimated rates. For example, a change can be detected if the difference between the current and previously estimated false fall detection rate for a sub-group exceeds a predetermined decision value. Alternatively, statistical tests can be performed to test for significant differences in the false fall detection rates using estimated confidence intervals.

If it is determined in step 320 that the false fall detection rates have not changed (beyond an acceptable amount), the method proceeds to step 330 wherein the current decision values employed by the fall detection algorithm are maintained (i.e. kept unchanged).

Conversely, if it is determined in step 320 that the false fall detection rates have changed (beyond an acceptable amount), the method proceeds to step 340 wherein new decision values are determined.

Here, a new decision value is calculated for each sub-group based on the obtained false fall detection rates such that the overall false fall detection rate is bounded (i.e. does not exceed) to a predetermined (acceptable) maximum. Thus, put more simply, step 340 comprises determining, based on the first false fall detection rate, a first decision value for distinguishing between a fall event and a non-fall-event of subjects of the first sub-group. Also, step 340 comprises determining, based on the second false fall detection rate, a second decision value for distinguishing between a fall event and a non-fall-event of subjects of the second sub-group.

For instance, determining the first decision value comprises determining a value at which a false fall detection rate for subjects of the first sub-group is equal to a predetermined rate.

In particular, a sub-group with a higher false fall detection rate will typically be assigned higher decision values.

In this example, the new decision values are calculated based on a constrained optimization procedure. The constraints on the decision values are introduced in the optimization to ensure a minimum detection probability for all groups.

By way of example, the optimization may be implemented in the following way:

For ease of notation, it is assumed that there are only two sub-groups of subject, namely a first sub-group A containing $N_A$ subjects and a second sub-group B comprising $N_B$ subscribers, respectively, where both $N_A$ and $N_9$ are integers greater than or equal one. First sub-group A has a measured false fall detection rate $FA_A$ and the second sub-group B has a measured false fall detection $FA_B$, for predetermined initial decision value $th_A$ and $th_B$.

A predetermined ROC curve (Receiver Operating Characteristic) is available. It is obtained, for example, by analysing laboratory (simulated) falls. The ROC curve is a function $$FP(th), TP(th) = \text{ROC}(th)$$

that takes as input a detection decision value th and returns as output a FP(th),TP(th) pair. Note that FP(th),TP(th) are the false positive and true positive rates per triggered event given decision value th. With the ROC curve, and given the measured/observed false alarm rate $FA_G$, it is possible to estimate the event trigger rate $Trg_G$ (the rate of occurrences of events that trigger the fall detection algorithm) for each group $$Trg_G = \frac{FA_G}{FP(th_G)}, \text{ with } G \in \{A, B\}.$$

Finally, the new decision values are found by solving the following optimization problem:

$$th_{A_{new}}, th_{B_{new}} = \underset{th_1, th_2}{\arg\min}(N_A * Trg_A * FP(th_1) + N_B * Trg_B * FP(th_2))$$

subject to $TP(th_1), TP(th_2) > TP_{min}$.

where $Trg_G$ are determined as given by the previous equation.

The optimization can also be formulated in a different but similar manner as the maximization of the detection probability while enforcing a constraint on the false fall detection rate.

After determining new first and second decision values in step 340, the method proceeds to step 350. In step 350, the newly-determined first and second decision values are associated with the first and second sub-groups, respectively. By way of example, this may entail updating decision values employed by subjects' fall detection devices and those stored in a database for example.

Although, in the above-described embodiment of FIG. 3, the step 310 of obtaining first and second false fall detection rates for first and second sub-groups is undertaken by monitoring the subjects and determining the first and second false fall detection rates, it will be appreciated that, in other embodiments, the first and second false fall detection rates for first and second sub-groups may simply be obtained from a separate and/or remotely-located information source (e.g. a fall detection system, database of fall cases, subject monitoring system, etc.). In this way, such alternative embodiments may be configured to simply receive information about fall detection rates for a monitored population of subjects, and then employ the received information to determine decision values for different sub-groups of the monitored population. An example could employ a look-up table, in which for given weather conditions/forecasts, a decision value is advised. Further, for weather conditions, the measured false fall detection rate in one location (e.g. state) may be used to predict the false fall detection rate in the neighboring state(s) to which a weather event (e.g. storm is moving). In this way, a determined decision value for a state may be used to update a decision value for a neighbouring to which the weather is travelling.

Also, it is noted that, from the above equations, the false fall detection rate (i.e. false alarm rate FA) can be expressed as Trg*FP. Thus, the false fall detection rate can be obtained 'indirectly' from the Trg*FP product and not by measuring an actual value (e.g. at the fall detector's output). The process of obtaining false fall detections rate can be undertaken 'indirectly' (i.e. calculated or determined from other values, such as calculated from a trigger rate or predicted from a neighbouring state for example.)

Further, in another embodiment, the step 320 of determining if the fall detection rates have changed may be omitted and the decision value always updated. In the case that the decision value do not change significantly, such updating may be effectively unnoticeable.

Strictly, for the test whether the FA-rate (decision values) have changed, a comparison value is needed. This is the outcome (330 and 350). Test can be on FA-rate per sub-group, or on effective total rate.

By way of further illustration of the proposed concept(s), a system for detecting a fall of a subject according to an embodiment will be now be described with reference to FIG. 4.

Figure 4:
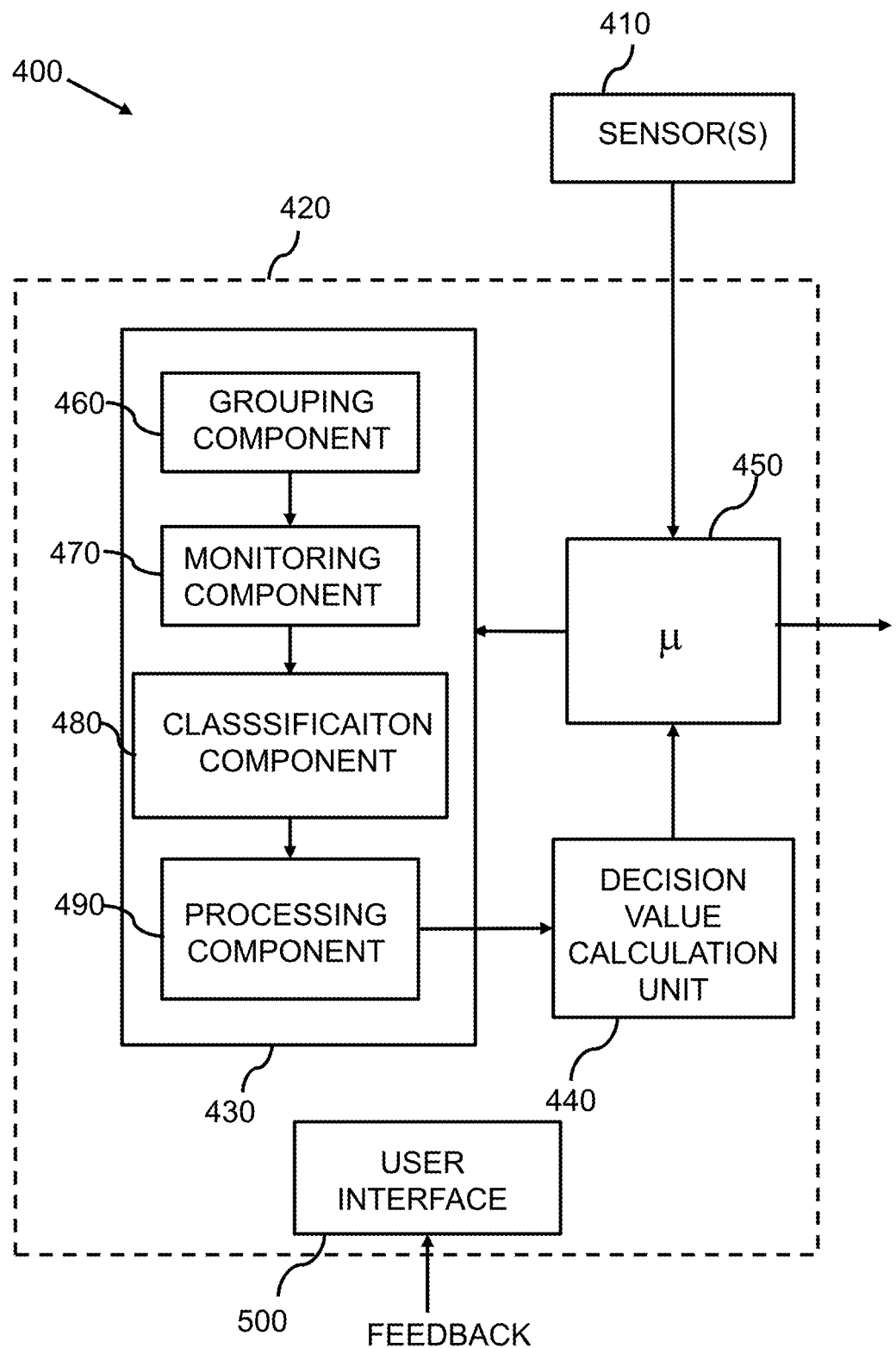
FIG. 4 illustrates a system for detecting a fall of a subject according to an exemplary embodiment.

FIG. 4 illustrates a system 400 for detecting a fall of a subject. The system 400 comprises one or more sensors 410 and a system 420 for distinguishing between a fall event and a non-fall-event for a plurality of subjects according to an embodiment of the invention.

The one or more sensors 410 are configured to obtain movement data responsive to the subject's movement. The one or more sensors may include at least one of an accelerometer, a barometric sensor, a tilt switch, a vibration sensor and a gyroscope. The one or more sensors may be part of a wearable device, for example, a smartwatch, a pendant worn around the neck or wrist, a pocket-carried device, an ear-worn device, etc.

The system 420 for distinguishing between a fall event and a non-fall-event for a plurality of subjects comprises an interface component 430, a decision value calculation unit 440 and a microprocessor 450 (i.e. a data processing unit). By way of example, the system 420 may be hosted on a sever (i.e. external and/or remote from the one or more sensors), and it may also be hosted in a distributed manner.

The interface component 430 is adapted to receive movement data from the one or more sensors 410 (via the microprocessor 450), and to detect events that occur in the movement data. An event may be detected when a defined trigger parameter (which may be a combination of parameters of the movement data) changes by more than a predetermined amount or when a value of the trigger parameter breaches a predetermined decision value. Other methods, including machine-learning and deep-learning approaches, would be apparent to the skilled person.

Further, the interface component 430 is adapted to obtain first and second false fall detection rates for first and second sub-groups of a plurality of subjects, respectively (e.g. from the cloud or a central data repository). As with the example of FIG. 3, the first and second sub-groups comprise subjects with first and second differing values of a property. In this example, the property comprises subject age, wherein a subject is deemed to have the first value of age if it has an age within the range 10-30 years and wherein a subject is deemed to have the second value of age if it has an age within the range 40-60 years.

More specifically, the interface component 430 of this example comprises a grouping component 460 configured to identify first and second sub-groups of the plurality of subjects. Put another way, the interface component groups subjects in sub-groups based on subject age.

The interface component 430 also includes a monitoring component 470 that is configured to monitor the plurality of subjects to detect potential fall events. Here, the monitoring component 470 receives movement data from the one or more sensors 410 (via the microprocessor 450), and detect potential fall events that occur in the movement data.

A classification component 480 of the interface component 430 is configured, for each detected potential fall event, to distinguish between the detected potential fall event being a fall event and a non-fall-event based on a fall detection algorithm employing a decision value. Put another way, the classification component 480 is configured to classify potential fall events as either a fall event and a non-fall-event, and this employs a threshold-based algorithm.

The interface component 430 also includes a processing component 490 configured to determine first and second false fall detection rates based on the identified first and second sub-groups and the results of distinguishing the potential fall events between being fall events and non-fall-events (provide by the classification component 480).

The first and second false fall detection rates obtained by the interface component are provided to the decision value calculation unit 440. The decision value calculation unit 440 is adapted to determine new values for the first and second decision values based on the first and second false fall detection rates, respectively.

More specifically, the decision value calculation unit 440 is adapted to determine, based on the first false fall detection rate, a first decision value for distinguishing between a fall event and a non-fall-event of subjects of the first sub-group. In doing so, the decision value calculation unit 440 is adapted to determine a value at which a false fall detection rate for subjects of the first sub-group is equal to a predetermined rate, e.g. a rate that maintains a predetermined minimum detection probability value (i.e. a minimum sensitivity).

Further, the decision value calculation unit 440 is adapted to determine, based on the second false fall detection rate, a second decision value for distinguishing between a fall event and a non-fall-event of subjects of the second sub-group. Here, the decision value calculation unit 440 is adapted to determine a value at which a false fall detection rate for subjects of the second sub-group is equal to the predetermined rate, such as the rate that maintains a predetermined minimum detection probability value (i.e. a minimum sensitivity).

The newly-determined decision values are passed from the decision value calculation unit 440 to the microprocessor 450. Based on movement data from the one or more sensors 410, the microprocessor 450 detects a potential fall event of a subject and determines which sub-group the subject is a member of. The microprocessor 450 is then configured to classify the detected potential fall event as a fall event or a non-fall event by comparing information associated with the fall event with the decision value for the sub-group the subject is determined to be a member of. The microprocessor 450 thus employs the decision values that are tailored to each sub-group in order to distinguish between a fall event and a non-fall event.

It is also noted that the system 400 of FIG. 4 comprises a user interface 500 that is configured to provide a feedback function. When activated, the feedback function instructs the system 400 for distinguishing between a fall event and a non-fall-event in order to re-classify a detected fall event as a non-fall event. This user feedback can then be used to update a false detection rate based on the re-classification of the event.

From the above description of exemplary embodiment, it will be understood that there is proposed a concept which adapts a fall detection decision value (e.g. threshold value) to different sub-groups of a monitored or subscriber population, and the sub-groups are defined according to a property or characteristic of a subject. By way of example, a property may comprise a physiological property or a physical property of subject, and such properties may have fixed or time-varying values.

The fall detection decision values may be determined so as to ensure a minimum detection probability. However, the variation of decision values across different subgroups may be such that an average over them yields an improved fall detection accuracy.

It will be understood that the disclosed methods are computer-implemented methods. As such, there is also proposed a concept of a computer program comprising code means for implementing any described method when said program is run on a processing system.

The skilled person would be readily capable of developing a processor for carrying out any herein described method. Thus, each step of a flow chart may represent a different action performed by a processor, and may be performed by a respective module of the processing processor.

As discussed above, the system makes use of a processor to perform the data processing. The processor can be implemented in numerous ways, with software and/or hardware, to perform the various functions required. The processor typically employs one or more microprocessors that may be programmed using software (e.g. microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted that the term "adapted to" is intended to be equivalent to the term "configured to". Any reference signs in the claims should not be construed as limiting the scope.

The invention claimed is:

1. A computer-based method for distinguishing between a fall event and a non-fall-event for a plurality of subjects, the method comprising:
    obtaining first and second false fall detection rates for first and second sub-groups of the plurality of subjects, respectively, and wherein the first and second sub-groups comprise subjects with first and second differing values of a property of the plurality of subjects, respectively;
    determining, based on the first false fall detection rate, a first decision value for distinguishing between a fall event and a non-fall-event of subjects of the first sub-group; and
    determining, based on the second false fall detection rate, a second decision value for distinguishing between a fall event and a non-fall-event of subjects of the second sub-group,
    wherein the fall detection rate for a sub-group of the plurality of subjects is based on a ratio between a number of false fall detections for the sub-group and the number of subjects in the sub-group.

2. The method of claim 1, wherein determining the first decision value comprises determining a value at which a false fall detection rate for subjects of the first sub-group is equal to a predetermined rate.

3. The method of claim 2, wherein the predetermined rate is defined so as to maintain a predetermined minimum detection probability value.

4. The method of claim 1, wherein the first and second decision values are determined so as to maintain an overall false fall detection rate across the first and second groups remains constant whilst the an average true positive detection rate is increased.

5. The method of claim 1, further comprising:
    associating the first decision value with each subject of the first sub-group; and associating the second decision value with each subject of the second sub-group.

6. The method of claim 1, wherein obtaining first and second false fall detection rates for first and second sub-groups of the plurality of subjects comprises:
identifying the first and second sub-groups of the plurality of subjects;
monitoring the plurality of subjects to detect potential fall events;
for each detected potential fall event, distinguishing between the detected potential fall event being a fall event and a non-fall-event based on a fall detection algorithm employing a decision value; and
determining first and second false fall detection rates based on the identified first and second sub-groups and the results of distinguishing the potential fall events between being fall events and non-fall-events.

7. The method of claim 1, wherein the property of the plurality of subjects comprises: location; activity; fall risk; age; medical condition; weight; gender; diagnosis; disease; prescription; or user equipment/aids.

8. A computer program comprising code means for implementing the method of claim 1 when said program is run on a processing system.

9. A system for distinguishing between a fall event and a non-fall-event for a plurality of subjects, the system comprising:
an interface component adapted to obtain first and second false fall detection rates for first and second sub-groups of a plurality of subjects, respectively, and wherein the first and second sub-groups comprise subjects with first and second differing values of a property of the plurality of subjects, respectively; and
a decision value calculation unit adapted to:
determine, based on the first false fall detection rate, a first decision value for distinguishing between a fall event and a non-fall-event of subjects of the first sub-group;
determine, based on the second false fall detection rate, a second decision value for distinguishing between a fall event and a non-fall-event of subjects of the second sub-group; and
determine a value at which a false fall detection rate for subjects of the first sub-group is equal to a predetermined rate.

10. The system of claim 9, wherein the predetermined rate is defined so as to maintain a predetermined minimum detection probability value.

11. The system of claim 8, further comprising an assignment unit configured to:
associate the first decision value with each subject of the first sub-group; and
associate the second decision value with each subject of the second sub-group.

12. The system of claim 8, wherein the interface component comprises:
a grouping component configured to identify the first and second sub-groups of the plurality of subjects;
a monitoring component configured to monitor the plurality of subjects to detect potential fall events;
a classification component configured, for each detected potential fall event, to distinguish between the detected potential fall event being a fall event and a non-fall-event based on a fall detection algorithm employing a decision value; and
a processing component configured to determine first and second false fall detection rates based on the identified first and second sub-groups and the results of distinguishing the potential fall events between being fall events and non-fall-events.

13. A system for detecting a fall of a subject, comprising:
one or more sensors for obtaining movement data responsive to a subject's movement;
the system for distinguishing between a fall event and a non-fall-event for a plurality of subjects of claim 9, further configured to:
receive the movement data from the one or more sensors;
detect a potential fall event based on the movement data;
determine which sub-group the subject is a member of; and
classify the detected potential fall event as a fall event or a non-fall event by comparing information associated with the fall event with the decision value for the sub-group the subject is determined to be a member of; and
a user interface configured to provide a feedback function, which, when activated, instructs the system for distinguishing between the fall event and the non-fall-event to re-classify a detected fall event as a non-fall event, and to update a false detection rate based on the re-classification of the event.

* * * * *